United States Patent [19]
Sannicolo et al.

[11] Patent Number: 6,153,758
[45] Date of Patent: Nov. 28, 2000

[54] HETEROARYLIC-ARYLIC DIPHOSPHINES AS CHIRAL LIGANDS

[75] Inventors: Francesco Sannicolo; Tiziana Benincori, both of Milan; Patrizia Antognazza, Locate Varesino; Serafino Gladiali, Sassari, all of Italy

[73] Assignee: Chemi S.p.A., Patrica, Italy

[21] Appl. No.: 09/308,420

[22] PCT Filed: Nov. 14, 1997

[86] PCT No.: PCT/EP97/06358

§ 371 Date: Apr. 18, 1999

§ 102(e) Date: Apr. 18, 1999

[87] PCT Pub. No.: WO98/22484

PCT Pub. Date: May 28, 1998

[30] Foreign Application Priority Data

Nov. 20, 1996 [IT] Italy ................................. MI96A2424

[51] Int. Cl.$^7$ ................................. C07F 9/28; C07F 9/02; C07D 337/00
[52] U.S. Cl. ............................... 548/111; 548/412; 549/6; 549/216
[58] Field of Search ...................... 549/6, 216; 548/111, 548/412

[56] References Cited

U.S. PATENT DOCUMENTS

| | | | |
|---|---|---|---|
| 5,739,396 | 4/1998 | Trost et al. | 564/15 |
| 5,907,045 | 5/1999 | Antognazza et al. | 549/7 |

FOREIGN PATENT DOCUMENTS

| | | |
|---|---|---|
| 0643065 | 3/1995 | European Pat. Off. . |
| WO92 16536 | 10/1992 | WIPO . |
| WO96 01831 | 1/1996 | WIPO . |

*Primary Examiner*—Deborah C. Lambkin
*Attorney, Agent, or Firm*—Collard & Roe, P.C.

[57] ABSTRACT

Diphosphines of a mixed heteroarylic-arylic type, wherein the phosphine group carrying backbone is constituted by the interconnection of a five-atom heteroaromatic ring and a carbocyclic aromatic ring, forming an atropoisomeric chiral system with a $C_1$ symmetry. Said chiral diphosphines are advantageously used as ligands for the formation of chiral complexes with transition metals, in particular Ru, Rh, Pd, Ir, Ni. The so-obtained chiral complexes are used as chiral complexes are used as chiral catalysts for stereocontrolled reactions, in particular diastereo and enantioselective reduction reactions, hydroformylation reactions, hydrosilylation reactions, hydrocyanation reactions, double-bond isomerisation reactions, other reactions of carbon—carbon bond formation.

42 Claims, No Drawings

HETEROARYLIC-ARYLIC DIPHOSPHINES AS CHIRAL LIGANDS

This appln is a 371 of PCT/EP97/06358 Nov. 14, 1997.

OBJECT OF THE INVENTION

The present invention relates to chiral diphosphines of a mixed heteroarylic-arylic type, the use of said diphosphines as ligands for transition metals, and complexes between said diphosphines and said transition metals.

The present invention also relates to the use of said complexes as chiral catalysts for stereocontrolled (stereoselective) reactions, such as for instance diastereo- and enantioselective reduction reactions, or asymmetric isomerisation reactions, hydroformylation reactions, hydrocyanation reactions as well as other reactions of carbon—carbon bond formation.

The present invention further relates to a process for the preparation of said chiral diphosphines of a mixed heteroarylic-arylic type, as well as to a process for the preparation of said complexes between said diphosphines and said transition metals.

Moreover, the present invention also relates to stereoselective reactions, such as for instance diastereo- and enenatioselective reductions, realised by using said chiral catalysts.

STATE OF THE ART

As is known, stereoselective reactions, and in particular stereocontrolled reductions such as for instance diastereo- and enantioselective hydrogenation reactions, are of great importance and have been studied for many years. Such reactions lead directly to the formation of optically active compounds which would be otherwise obtainable only as racemes to be submitted to resolution in the individual enatiomers according to conventional techniques. In these cases, there takes place a simultaneous formation of identical quantities of the undesired enantiomer which must be, removed and/or reconverted. The realisation of stereoselective reactions has allowed to eliminate most of the aforementioned problems, opening therefore a research field of great interest.

Generally, stereocontrolled reactions realised, for instance, by means of chiral catalysts, allow to obtain optically active reaction products, often with good enantiomeric excesses. Chiral catalysts of a known type utilised in this field, and particularly for stereocontrolled reduction reactions, are for instance constituted by complexes between transition metals and chiral phosphines such as DIPAMP [KNOWLES W. S. et al., J.Chem.Soc. chem. Commun. 10 (1972); VINEYARD B. D. et al., J.Am.Chem.Soc. 99, 5946(1977)] or CHIRAPHOS [FRYZUK M. D. et al., J.Am.Chem.Soc. 99, 6562(1977)]. Other examples of chiral phosphines include for intance BINAP, BIPHEMP, BICHEP [NOYORI T. et al., J.Am.Chem.Soc. 102, 7932(1980); SCHMID R. et al., Helv.Chim.Acta 71, 897(1988); MIYASHITA A. et al., Chem.Lett. 1849(1989)]. The latter are phosphines whose chirality is due to the presence of an atropoisomeric diaryl system ($C_2$ symmetry system), and they have been utilised for the preparation of very efficient chiral systems; however, the phosphine synthesis process is rather complex and comprises many complicated steps, and accordingly the corresponding chiral catalysts are very expensive.

There are also described [WO 96/01831, by the same Applicant] chiral diphosphines constituted by a biheterocyclic 5-atom aromatic system ($C_2$ symmetry atropoisomeric system) which, by complexation with transition metals, form very efficient chiral catalysts); the aforesaid diposphines are prepared according to synthesis processes simpler compared with those utilised for BINAP, BIPHEMP and BICHEP, and consequently the corresponding chiral catalysts are less expensive. In spite of this, the synthesis processes of the aforesaid chiral diphosphines of a diheterocyclic type are still rather complicated, as they require many steps; besides, the above processes only allow to prepare chiral phosphines wherein the two phosphorous atoms carry substituents that are always equal to one another.

There are also known chiral catalysts constituted by complexes between $C_1$ symmetry phosphine systems and transition metals; these catalysts, while being generally less expensive, are also often less efficient than the corresponding $C_2$ symmetry catalysts, as different, non equivalent catalyst species may generate in the reaction environment, which can give rise to opposed stereoselectivities.

OBJECT OF THE INVENTION

Object of the present invention is to provide a chiral diphosphine that is easily accessible from the synthetic point of view compared to the chiral diphosphines of the known type.

Another object of this invention is to provide a chiral diphosphine that is advantageous from the economic point of view.

A further object of this invention is to provide a chiral diphosphine for use as a ligand for transition metals for the formation of particularly stable co-ordination bonds.

Still another object of this invention is to provide a process of preparation of chiral diphosphines that comprises simple steps, has contained costs and industrial applicability.

Still a further object of this invention is to provide a process of preparation of said chiral diphosphines that allows to realise said diphosphines with substituents other than phosphorus atoms.

Still a further object of this invention is to provide a complex between said chiral diphosphines and said transition metals that is stable and suitable for use as chiral catalyst for stereocontrolled reactions.

Another object of this invention is to provide a chiral catalyst for stereocontrolled reactions that is highly reactive and allows to obtain a high regio-, chemo-, diastereo- and enatioselectivity.

Still another object of this invention is to provide a chiral catalyst for stereocontrolled reactions that allows to operate in mild reaction conditions, keeping however high reaction velocities.

A further object of this invention is to realise stereocontrolled reactions, in particular reduction and isomerisation reactions that involve the use of said chiral catalysts and lead to the formation of optically active products with high diastereisometric or enantiometric excesses.

DESCRIPTION OF THE INVENTION

These and still other objects and related advantages that will be better clarified later on, are achieved by a chiral heteroarylic-arylic diphosphine of a mixed type of the following general formula:

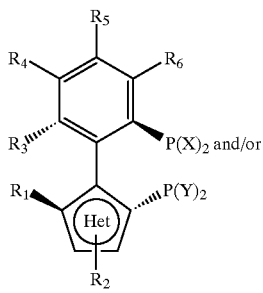

(IA)

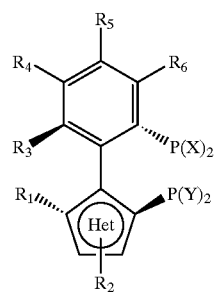

(IB)

wherein:

X=Y or X≠Y, and X, Y are selected from among linear or branched $C_3$–$C_{10}$ alkyl, cyclic $C_5$–$C_6$ alkyl, phenyl, aryl, substituted phenyl or aryl, wherein the substituents are selected from among linear or branched $C_1$–$C_{10}$, halogen, $OR_7$, wherein $R_7$ is hydrogen, linear or branched $C_1$–$C_{10}$ alkyl;

$R_1$ is selected from among linear or branched $C_1$–$C_{10}$ alkyl, cyclic $C_5$–$C_6$ alkyl, $OR_{11}$, with $R_{11}$ selected equal to hydrogen, linear or branched $C_1$–$C_{10}$ alkyl, $NR_{12}R_{13}$, wherein $R_{12}$ and $R_{13}$ may be equal or different, and selected from among linear or branched $C_1$–$C_{10}$ alkyl, phenyl, aryl, substituted phenyl or aryl, wherein substituents are selected from among linear or branched $C_1$–$C_{10}$ alkyl, halogen, $OR_7$, wherein $R_7$ is hydrogen, linear or branched $C_1$–$C_{10}$ alkyl;

$R_2$ is selected from among hydrogen, linear or branched $C_1$–$C_{10}$ alkyl, cyclic $C_5$–$C_6$ alkyl, phenyl, aryl, substituted phenyl or aryl, wherein substituents are selected from among linear or branched $C_1$–$C_{10}$ alkyl, halogen, $OR_7$, wherein $R_7$ is hydrogen, linear or branched $C_1$–$C_{10}$ alkyl;

$COOR_{10}$, wherein $R_{10}$ is linear or branched $C_1$–$C_{10}$ alkyl, $NR_{12}R_{13}$, wherein $R_{12}$ and $R_{13}$ may be equal or different, and selected from among linear or branched $C_1$–$C_{10}$ alkyl, $OR_{11}$ with $R_{11}$ selected as equal to hydrogen, linear or branched $C_1$–$C_{10}$ alkyl;

or the 5-atom heterocyclic aromatic ring is condensed to a benzene ring or a substituted or non substituted naphthalene ring, wherein the substituents are selected from among linear or branched $C_1$–$C_{10}$ alkyl, cyclic $C_5$–$C_6$ alkyl, halogen, and in this case either $R_1$ or $R_2$ or the both of then may be part of said benzene or naphthalene ring, and the carbocyclic aromatic ring is condensated to a benzene ring or a possibly substituted naphthalene ring wherein the substituents are selected from among linear or branched $C_1$–$C_{10}$ alkyl, cyclic $C_5$–$C_6$ alkyl, halogen and the carbocyclic aromatic ring is condensated to a benzene ring or a possibly substituted naphtalene ring wherein the substituents are selected from among linear or branched $C_1$–$C_{10}$ alkyl, cyclic $C_5$–$C_6$ alkyl, halogen;

$R_3$, $R_4$, $R_5$, $R_6$ may be equal or different and are selected from among hydrogen, linear or branched $C_1$–$C_{10}$ alkyl, cyclic $C_5$–$C_6$ alkyl, halogen, $OR_{11}$ with $R_{11}$ selected as equal to hydrogen, linear or branched $C_1$–$C_{10}$ alkyl, $SO_3H$ or a corresponding salt, $NR_{12}R_{13}$ wherein $R_{12}$ and $R_{13}$ may equal or different, and selected from among linear or branched $C_1$–$C_{10}$ alkyl, or $R_{12}$ and $R_{13}$ form with the N atom a morpholinic, pyrrolidonic, piperidinic ring;

or a couple of the adjoining $R_3$ to $R_6$ substituents represents a benzene ring wherein the substituents are chosen from among linear or branched $C_1$–$C_{10}$ alkyl, cyclic $C_5$–$C_6$ alkyl, halogen, condensated to the aryl ring of said diphosphine.

The atropoisomeric chiral diphosphine of mixed heteroacrylic-arylic type of the formula (IA), (IB), according to the present invention is substantially characterised by a heteroarylic system of a mixed type, constituted by the radical of a 5-atom heterocyclic aromatic ring, possibly substituted and/or condensated, united to the radical of an aromatic carbocyclic ring, also possibly substituted and/or condensated. The energy rotation barrier around the bond that unites the heterocyclic system to the carbocyclic system must be such as to allow the separation of the two optical antipodes.

In particular, always according to the present invention, said radical of said 5-atom heterocyclic aromatic radical is selected from among:

furyl thienyl pyrrolyl 2-imidazolyl and the corresponding benzocondensates, 5- pirazolyl 2-[1,3,4-triazolyl]

4-thiazolyl 4-isoxazolyl.

Always according to the present invention, heteroarylic-arylic chiral diphosphines having the following formulae were found to be particularly advantageous:

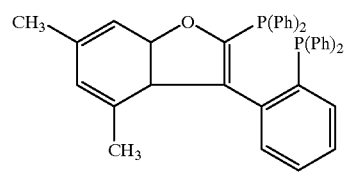

(IIA,IIB)

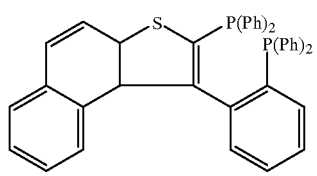

(IIIA,IIIB)

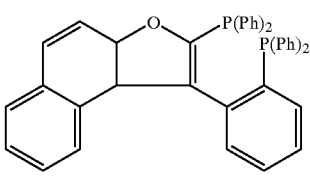

(IVA,IVB)

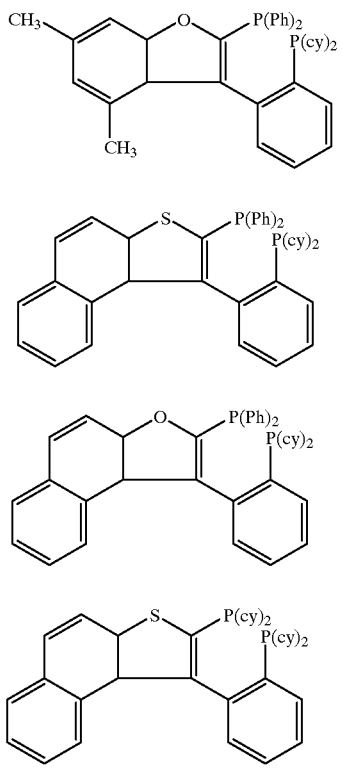

(VA,VB)

(VIA,VIB)

(VIIA,VIIB)

(VIIIA,VIIIB)

where cy means cyclohexyl.

According to the present invention, the diphosphine of the general formula (IA), (IB), is a $C_1$ symmetry atropoisomeric chiral system, wherein the backbone carrying the phosphine groups is constituted as said hereinanbove, by the interconnection of a 5-atom heteroaromatic ring and a carbocyclic ring.

Thanks to their structural characteristics, the diphosphines according to the invention may be synthesised by means of very simple processes, comprising a limited number of steps and which allow to obtain high yields of phosphines of high purity and to extremely advantageous costs.

Besides, as they are heterocyclic systems of a mixed type, it is possible to realise chiral diphosphines having the formula (IA), (IB), wherein the X and Y groups are different from one another and may be therefore suitably selected, according to the intended use of diphosphine. For instance, the diphosphines having the formula (VA, VB), (VIA, VIB), (VIIA, VIIB), object of the present invention, were found to be particularly advantageous.

On the contrary, in the atropoisometric chiral diphosphine systems according to the known art, the substituents of the phosphorus atoms must necessarily be equal to one another, as these systems have a $C_2$ symmetry.

The chiral diphosphine of the formula (IA), (IB) have proved to be very advantageous when used as ligands in the formation of complexes with transition metals; in particular, said complexes are stable and, besides, they are prepared with simple and effective processes. As the diphosphine that acts as a reactant is synthesised, as said above, by means of processes that are very advantageous from the economic point of view, also the corresponding chiral complex obtained by complexation with a transition metal results to be economically advantageous, especially if compared with the costs of chiral complexes realised by means of diphosphines according to the known art.

The above chiral complexes of the diphosphines of formula (IA), (IB) according to the present invention with transition metals are used as chiral catalysts in stereocontrolled reactions and in particular in diastero- and enantioselective reduction reactions and isomerisation reactions. Said catalysts proved surprisingly effective as they are very active and have high stereoselection capacities.

The chiral catalysts according to the known art, constituted by complexes between $C_2$ symmetry chiral diphosphines and transition metals, while being rather effective when used to carry out stereocontrolled reactions, as has been already said, are very expensive and, consequently, their use is rather onerous.

The chiral catalysts always according to the known art, but constituted by complexes between $C_1$ symmetry diphosphine systems of a known type and transition metals, while being less expensive and therefore more advantageous from the economic point of view than the catalysts comprising $C_2$ symmetry diphosphines of a known type, may prove poorly effective, as in the reaction environment there may generate different, non equivalent catalytic species that may give rise to opposite stereoelectivities.

On the contrary, the chiral catalysts according to the present invention, constituted by complexes between chiral diphosphines of formula (IA) (IB) and transition metals, while being all the same $C_1$ symmetry systems, have proved to be, not only very advantageous from the economic point of view, but also surprisingly effective, giving rise to a high degree of stereoselection, and may therefore be advantageously utilised in stereoselective reactions, ensuring a high degree of stereoselection and very limited costs.

The eteroarylic-arylic chiral diphosphines of formula (IA) (IB) of the present invention may be advantageously prepared, for instance, according to the following synthesis scheme, that includes the following steps:

synthesis according to methods of a known type of an ortho-halogen-arylheterocyclic system, wherein the heterocyclic system has the position adjoining the inter-ring metallable bond, a first metallation reaction of said position adjoining the inter-ring bond or metal-halogen exchange reaction of halogen on the aryl ring, obtaining a metallated arylheterocyclic system, reaction of said metallated system with a chlorophosphine or a phosphinyl chloride, obtaining a phosphinic heteroaryl system or a phosphinylic heteroaryl system, a second reaction of metal-haloaen exchange of halogen on the arylic ring or metallation reaction of said position adjoining the inter-ring bond, obtaining a hetercaryl phosphinic system or a heteroaryl phosphinylic metallated system, reaction of said heteroaryl phosphinic system or heteroaryl phosphinylic metallated system with a chlorophosphine or a phosphinyl chloride, obtaining a heteroaryldiphosphinic, heteroarylphosphinylic or heteroaylphosphinic phosphinylic racemic system, possible conversion of said heteroaryldiphosphinic, heteroarylphosphinylic or heteroaylphosphinic phosphinylic racemic system into a heteroaryldiphosphinylic racemic system by oxidation reaction according to known techniques, reaction of said heteroaryldiphosphinylic racemic system with an acid resolving chiral agent, obtaining two diastereoisomeric adducts, separation of said diastereoisomeric adducts by fractionated crystallisation, basic treatment of each of said separated diastereoisomeric adducts, obtaining the corresponding enantiomerically pure heteroaryldiphosphinylic system, reduction of said enantiomerically pure heteroaryldiphosphinylic system with reducing agents of a known type, obtaining an enantiomerically pure heteroaryldiphosphinic chiral system (IA) (IB).

Always according to the present invention, said metallation and metal-halogen exchange reactions may also take place simultaneously, obtaining a bis-metallated system. In this case, there is directly obtained, by reaction of said bis-metallated system with chlorophoschine or phosphinyl chloride, a heteroaryldiphosphinic or heteroaryldiphosphinylic racemic system, which is subsequently treated as described above.

According to the process of the present invention, the reducing agents are advantageously selected, for instance, among silanes; besides, said diphosphinic racemic system may also be advantageously resolved directly by column chromatography utilising chiral means, such as for instance, the stationary phase, the eluent system, and the like. Always in case of formation of said diastereoisomeric adducts according to the invention, the acid resolvent chiral agent is preferably selected, for instance, among dibenzoyltartaric acid, ditolyltartaric acid, camphosulfonic acids, and the like.

The above described process allows, when the metallation reaction is carried out in subsequent stages, to synthesise heteroarylic-arylic diphosphines of general formula (IA) (IB), wherein X≠Y; as said, diphosphines of this type are not available in case of $C_2$ symmetry systems according to the known art. On the contrary, in case of chiral diphosphines (IA) (IB) wherein X=Y, the process may be more conveniently realised by simultaneous metallation of the two positions and reaction with chlorophosphine or phosphinyl chloride, obtaining directly a heteroaryldiphosphinic or heteroaryldiphosphinylic system. The above described process does not exclude alternative sequences known to those skilled in the art.

As said, the heteroaryldiphosphinic system objet of the present invention is used as a ligand for the complexation of transition metals, such as for instance Ru, Rh, Pd, Pt, Ir, Ni, obtaining chiral complexes that are in their turn used as catalysts for stereocontrolled reactions. Always according to the present invention, said chiral complexes are preferably obtained by exchange reaction between the heteroaryldiphosphinic system and a complex of the selected metal, wherein the bond between the metal and the ligand is more labile than the one which will form between the metal and the heteroaryldiphosphinic system; in this way, the heteroaryldiphosphinic system will replace the ligand in the co-ordination to the metal, forming a preferred co-ordination bond. In the above exchange reaction, the metal is used in co-ordination with ligands such as for instance 1,5-cis,cis-cyclooctadiene, norbonadiene, (ethylene)$_2$, triarylstilbene, benzonitrile, bismetallyl and the like. The complex constituted by the selected metal and the ligand is dissolved in a suitable solvent; afterwards, the heteroaryldiphosphinic system is added in either the solid state or in a solution of a suitable solvent. The reaction progress and therefore the formation of the complex is controlled through the examination of possible colour variations, or also by means of a spectroscopic type, for instance $^{31}$P-NMR, or analytical methods, such as GC. Upon completion of the reaction, the solvent is removed and the so obtained chiral complex may be utilised as such or it may be submitted to a further purification according to known techniques. The solvents preferably used for the preparation of said chiral complexes are, for instance, chlorinated solvents, alcohols, aromatic hydrocarbons, ethers, dimethyl formamide. The chiral complexes according to the present invention are preferably prepared at the time when they have to be used as chiral catalysts in the stereocontrolled reactions.

The stereoselective reactions realised with the chiral complexes of the present invention as chiral catalysts are characterized by high reaction speeds, mild reaction conditions, for instance as concerns pressure and temperature conditions and the amount of catalyst used, and besides they provide the possibility of utilising low ecological impact solvents.

Always according to the present invention, the chiral complexes of the invention are advantageously used, as said, as catalysts in stereocontrolled reaction and in particular diastereo- and enationselective reaction, such as for instance, reduction of olefins (—C=C—), reduction of ketone carbonyl groups (—C=O), reduction of imine groups (—C=N—), reduction of enamines (—N—C=C—), obtaining optically active compounds with high diastereoisomeric and enantiomeric ecesses. Always according to the present invention, said chiral catalysts are also advantageously used to realize hydroformylation reactions, hydroboration reactions, hydrosilylation reactions, hydrocyanation reactions, other reactions of carbon—carbon bond formation and double bond isomerisation reactions.

Solely by way of non limiting example of the present invention, some examples of practical realization are described in the following, and in particular there is described the preparation of some heteroarylic-arylic chiral diphosphines according to the invention, the preparation of some chiral complexes between said diphosphines and the metals Ru and Rh, as well as the use of said complexes as chiral catalysts per the realization of stereoselective reactions.

EXAMPLE 1

Preparation of 3-[(2-diphenylphosphino)phenyl]-2-diphenyl phosphino-4,6-dimethyl[b]furan (IIA, IIB)

a) Preparation of 1-[(2-bromo)phenyl]-2-(3,5-dimethyl phenoxy) ethanone

A solution of MeONa in methyl alcohol, obtained by dissolving metallic sodium (1 g) in methyl alcohol (15 ml) was dripped in a solution of 3,5-dimethylphenol (4.39 g) in methyl alcohol. The reaction mixture was stirred for 30 minutes and the solvent removed under reduced pressure. A solution of 1-[(2-bromo)phenyl]-2-bromoethanone (10 g), obtained as described by R. E. LUTZ et al., J.O.C. vol. 12, p. 617 (1947) in DMF (30 ml) was dripped in a solution of the sodium salt (5.2 g), prepared as described hereabove, in DMF (50 ml) and the reaction mixture was stirred for 3 days. The solvent was removed under reduced pressure; the residue was treated with $H_2O$ and exhaustively extracted with methylene chloride. The united organic phases were anhydrified ($Na_2SO_4$) and the solvent was removed under reduced pressure. The reaction raw product was chromatographied, using a mixture of hexane-methylene chloride 6:4 (v/v) as eluent. From the intermediate fractions a solid was obtained which, dissolved in isopropyl ether, produced pure 1-[(2-bromo)phenyl]-2-(3,5-dimethylphenoxy)ethanone (0.7 g, m.p.=74° C.) with 50% yields. 3,5-dimethylphenol was obtained from the tail fractions.

$^1$H NMR (CDCl$_3$): 2.26 (6H, s), 5.1 (2H, s), 6.52 (2H, s), 6.63 (1H, s), 7.35 (1H, d), 7.4 (1H, t), 7.48 (1H, dd), 7.61 (1H, d).

b) Preparation of 3-[(2-bromo)phenyl]-4,6-dimethylbenzo[b]furan

1-[(2-bromo)phenyl]-2-(3,5-dimethylphenoxy)ethanone (1.3 g) was added under vigorous stirring to polyphosphoric acid (PPA) (13 g) preheated at 80° C. and the reaction mixture was stirred for 30 minutes. Then, the reaction mixture was poured in $H_2O$, brought to an alkaline pH with $NH_3$ and exhaustively extracted with methylene chloride. The united organic phases were washed with water, anhydrified ($Na_2SO_4$) and the solvent was removed under reduced pressure. The residue was chromatographied, using hexane as eluent. 3-[(2-bromo)phenyl]-4,6dimethylbenzo[b]furan (1.1 g) was obtained from the head fractions.

$^1H$ NMR ($CDCl_3$) (ppm): 2.1 (3H, s, $CH_3$), 2.43 (3H, s, $CH_3$), 6.82 (1H, s), 7.29 (4H, m), 7.47 (1H, s), 7.68 (1H, d).

c) Preparation of 3-[(2-diphenylphosphinyl)phenyl]-2-diphenylphosphinyl-4,6-dimethylbenzo[b]furan A solution 1.6M of BuLi in hexane (5.2 ml) was dripped in a solution of 3-[(2-bromo)phenyl]-4,6-dimethylbenzo[b]furan (1.15 g) and TMEDA (1.2 ml) in THF (100 ml), cooled at −70° C. The reaction was exothermic and the temperature reached −50° C. The temperature was allowed to increase up to 20° C. and the reaction mixture was stirred for 30 minutes at this temperature. Diphenylchlorophosphine (0.9 g) was then added an the reaction mixture was stirred for 3 hours. The solvent was removed under a reduced pressure; $H_2O$ (20 ml), $CH_2Cl_2$ (100 ml) and $H_2O_2$ (5 ml) was added and the reaction mixture was stirred for 2 hours. After the phase separation, the aqueous phase was extracted several times with methylene chloride. The united organic phases were anhydrified ($Na_2SO_4$) and the solvent was removed under reduced pressure. The residue was chromatographed using a mixture AcOEt-$CH_2Cl_2$ 3:7 (v/v) as eluent 3-[(2-diphenylphosphinyl)phenyl]-2-diphenylphosphinyl-4,6-dimethylbenzo[b]furan (1. g, m.p.=218° C.) was obtained from the tail fractions.

$^1H$ ($CDCl_3$) (ppm): 1.97 (3H, s, $CH_3$), 2.17 (3H, s, $CH_3$), 6.61 (1H, s), 7.02 (1H, s), 7.48 (14H, m), 7.7 (6H, m), 7.89 (4H, m), 7.7 (6H, m), 7.89 (4H, m).

d) Preparation of 3-[(2-diphenylphosphino)phenyl]-2-diphenyl phosphino-4,6-dimethylbenzo[b]furan (IIA, IIB)

EXAMPLE 2

Preparation of 3-[(2-diphenylphosphino)phenyl]-2-diphenyl phosphino-naphthothiophene (IIIA, IIIB)

a) Preparation of 1-[(2-bromo)phenyl]-2-naphthyl)thioethanone

A solution of MeONa in methyl alcohol, obtained by dissolving metallic sodium (0.96 g) in methyl alcohol (15 ml) was dripped in a solution of 2-thianaphthol (5.5 g) in methyl alcohol. The reaction mixture was stirred for 30 minutes and the solvent was removed under reduced pressure. A solution of 1-[(2-bromo)phenyl]-2-bromoethanone (10 g) in DMF was added to a solution of the sodium salt (6.2 g), prepared as described above in DMF (30 ml). The reaction was exothermic and instantaneous. The solvent was removed under reduced pressure and the reaction raw product was treated with $H_2O$ and methylene chloride. The united organic phases were anhydrified ($Na_2SO_4$) and the solvent was removed under reduced pressure. The reaction raw material was chromatografied using a hexane-methylene chloride 4:6 (v/v) mixture as eluent. 1-[(2-bromo)phenyl]-2-(2-naphthyl)thio-ethanone (4.0 g) was obtained from the head fractions.

$^1H$ NMR ($CDCl_3$): 7.28 (3H, m), 7.46 (4H, m), 7.72 (4H, m).

b) Preparation of 3-[(2-bromo)phenyl]-naphthothiophene

1-[(2-bromo)phenyl]-2-(2-naphthyl)thio-ethanone (0.5 g) was added under vigorous stirring to a portion of PPA (7.28 g) preheated to 80° C. The reaction mixture was stirred at 80° C. for 2 hours, then poured on ice and brought to an alkaline pH with ammonia. The organic phase was exhaustively extracted with methylene chloride. The collected organic phases were washed with water, anhydrified ($Na_2SO_4$) and the solvent was removed under reduced pressure. The residue was chromatographied utilising a methylene chloride-hexane 1:1 (v/v) mixture. 3-[(2-bromo)phenyl]-naphthothiophene (6.0 g, m.p.=99° C.) was obtained from the head fractions.

$^1H$ NMR ($CDCl_3$) (ppm): 7.28 (1H, t), 7.38 (1H, s), 7.48 (5H, m), 7.78 (2H, d), 7.93 (2H, d).

c) Preparation of 3-[(2-diphenylphosphinyl)phenyl-2-diphenylphosphinyl-naphthothiophene A solution of 1.6M of BuLi in hexane (8 ml) was dripped in a solution of 3-[(2-bromo)phenyl]-naphthothiophene (2 g) and TMEDA (2 ml) in THF (50 ml), cooled at −70° C. The reaction was exothermic and the temperature reached −50° C. The temperature was allowed to increase up to 20° C. and the reaction mixture was stirred for 1 h at this temperature. Diphenylchlorophosphine (2.4 ml) was added to the reaction mixture which was stirred overnight. The solvent was removed under reduced pressure, $H_2O$ (2 ml), $CH_2Cl_2$ (50 ml) and $H_2O_2$ (6 ml) was added to the residue and the reaction mixture was stirred for 2 hours. After the phase separation, the aqueous phase was exhaustively extracted with methylene chloride; the united organic phases were anhydrified ($Na_2SO_4$) and the solvent was removed under reduced pressure. The residue was chromatographied, USING an AcOEt-$CH_2Cl_2$ 3:7 (v/v) mixture as eluent. 3-[(2-diphenyl phosphinyl)phenyl]-2-diphenylphosphinyl-napthothiophene (1.1 g; m.p.=303° C.) was obtained from the tail fractions.

$^1H$ NMR ($CDCl_3$) (ppm): 7.34 (m, 30H).
$^{31}P$ NMR ($CDCl_3$): 20.4 (s, 1P), 28 (s, 1P).

d) Preparation of 3-[(2-diphenylphosphino)phenyl]-2-diphenylphosphino-napthothiophene (IIIA, IIIB)

Trichlorosilane (2 ml) was added under stirring to a solution of 3-[(2-diphenylphosphinyl)phenyl]-2-diphenylphosphinyl-naphtho thiophene (1 g) in xylene (20 ml) and triethylamine (2.8 ml), kept in argon atmosphere. The reaction mixture was heated to 110° C. under stirring for 6 h and treated with degassed water. The aqueous phase was extracted several times with degassed methylene chloride. The collected organic phases were anhydrified ($Na_2SO_4$) and the solvent was removed under reduced pressure. The residue was dissolved in methyl alcohol to give 3-[(2-diphenylphosphino)phenyl]-2-diphenylphosphino-napthothiophene (IIIA, IIIB) (0.9 g; m.p.=190° C.).

$^{31}P$ NMR ($CDCl_3$): −24.96 (s, 1P), −14.09 (s, 1P).

EXAMPLE 3

Preparation of 3-[(2-diphenylphosphino)phenyl]-2-diphenylphosphino-naphthofuran (IVA, IVB)

a) Preparation of 1-[(2-bromo)phenyl]-2-(2-naphthyl)oxy-ethanone

A solution of MeONa in methyl alcohol, obtained by dissolving metallic sodium (3 g) in methyl alcohol (25 ml) was dripped in a solution of 2-naphthol (25 g). The reaction mixture was stirred for 30 minutes and the solvent removed under reduced pressure. A solution of 1-[(2-bromo)phenyl]-2-bromo-ethanone (21 g) in DMF (50 ml) was dripped in a solution of the sodium salt (16.5), prepared as described above, in DMF (100 ml) and the reaction mixture was stirred for 3 days. The solvent was removed under reduced pressure; the residue was treated with $H_2O$ and exhaustively extracted with methylene chloride. The united organic phases were anhydrified ($Na_2SO_4$) and the solvent was removed under reduced pressure. The reaction raw material was chromatohraphied using chloroform as eluent. 1-[(2-bromo)phenyl]-2-(2-naphthyl)oxy-ethanone was obtained from the tail fractions (16 g, yield 62%).

$^1$H NMR (CDCl$_3$) (ppm): 5.22 (s, 2H), 7.39 (m, 11H).

b) Preparation of 3-[(2-bromo)phenyl]-naphthofuran

1-[(2-bromo)phenyl]-2-(2-naphthyl)oxy-ethanone (16 g) was added under vigorous stirring to polyphosphoric acid (PPA) preheated at 80° C. and the reaction mixture was stirred for 1 h and 30 minutes. The reaction mixture was poured in $H_2O$, brought to an alkaline pH with $NH_3$ and exhaustively extracted with methylene chloride. The united organic phases were washed with water, anhydrified ($Na_2SO_4$) and the solvent was removed under reduced pressure to give 3-[(2-bromo)phenyl]-napthofuran (11 g, yield 72%).

$^1$H NMR (CDCl$_3$) (ppm): 7.48 (m, 7H), 7.77 (m, 3H), 7.96 (d, 1H).

c) Preparation of 3-[(2-diphenylphosphinyl)phenyl]-2-diphenylphosphinyl-naphthofuran A solution 1.6M of BuLi in hexane (25 ml) was dripped in a solution of 3-[(2-bromo)phenyl]-naphthofuran (5.78 g) and TMEDA (6 ml) in THF (100 ml), cooled at −70° C. The reaction was exothermic and the temperature reached −50° C. The temperature was allowed to increase up to 20° C. and the reaction mixture was stirred for 30 minutes at this temperature. Diphenylphosphine (7.4 ml) was added and the reaction mixture was stirred for 1 h. The solvent was removed under reduced pressure; $H_2O$ (20 ml), $CH_2Cl_2$ (100 ml) and $H_2O_2$ (20 ml) was added to the residue. The reaction mixture was stirred for 2 h. After the phase separation, the aqueous phase was extracted several times with methylene chloride. The collected organic phases were anhydrified ($Na_2SO_4$) and the solvent was removed under reduced pressure. The residue was chromatographied using an AcOEt/$CH_2Cl_2$ 3:7 (v/v) as eluent. 3-[(2-diphenylphosphinyl)phenyl]-2-diphenylphosphinyl-2-diphenylphosphinyl-naphthofuran (6 g, m.p.=155–165° C.).

$^1$H NMR (CDCl$_3$) (ppm): 6.63 (2H, m), 7.35 (20H, m), 7.78 (8H, m).

$^{31}$P NMR (CDCl$_3$): 18.90 (s, 1P), 31.85 (s, 1P).

d) Preparation of 3-[(2-diphenylphosphino)phenyl]-2-diphenylphosphino-naphthofuran Trichlorosilane (10.6 ml) was added under stirring to a solution of 3-[(2-diphenylphosphinyl)phenyl]-2-diphenylphosphinyl-naphthofuran (6 g) in xylene (50 ml) and triethylamine (12.5 ml), kept in argon atmosphere. The reaction mixture was stirred for 1 h at 100° C., 1 h at 120° C. and 3 h at 140° C. the reaction mixture was treated with degasses water; the aqueous phase was extracted several times with degassed methylene chloride. The collected organic phases were anhydrified ($Na_2SO_4$) and the solvent was removed under reduced pressure. The residue was dissolved in argon atmosphere with degassed methyl alcohol to give 3-[(2-diphenylphosphino)phenyl]-2-diphenylphosphino-naphthofuran (IVA, IVB) (4.2 g, yield= 72%).

$^{31}$P NMR (CDCl$_3$): −32.10 (1P, s), −13.72 (1P, s).

$^1$H NMR (CDCl$_3$) (ppm): 6.93 (2H, t), 7.32 (25H, m), 7.62 (1H, d), 7.75 (1H, d), 7.91 (1H, d).

EXAMPLE 4 a) Resolution: (+)-3-[(2- diphenylphosphinyl)phenyl]-2-diphenylphosphinyl-naphthothiophene (IIIA, IIIB)

1.71 g of a mixture of racemic diphosphine oxide as obtained in point c) of Example 2, and 0.975 g of (−)-o,o'-dibenzoyl-L-tartaric acid (DBTA) was heated dissolved in 60 ml of a mixture composed by AcOEt/CHCl$_3$ 35:25 (v/v). After 25 h at room temperature there was obtained by filtration 1.078 g of an adduct (V) between diphosphinoxide (+) and DBTA (−), with $[\alpha]_D^{25}$=+60.5° (c=0.35 in EtOH).

1.043 g of adduct (V) between diphosphinoxide (+) and DBTA (−) was heated and dissolved in 38.5 ml of a mixture constituted by AcOEt/CHCl$_3$ 22.5:16 (v/v). After 25 h at room temperature there was obtained by filtration 0.973 g of an adduct (V) between diphosphinoxide (+) and DBTA (−), with a m.p.=165–185° C. and $[\alpha]_D^{25}$=+64.7 ° (c =0.36 in EtOH).

b) Deblocking of the adduct (V) of the preceding point 0.973 g (V) of adduct were treated with 16 ml of NaOH and the mixture was extracted twice with 2 portions of 20 ml each of $CH_2Cl_2$. The so obtained organic phases were united, washed with 20 ml of water and dried on $Na_2SO_4$. The mixture was filtered, the solvent was evaporated under reduced pressure and 0.5 g of optically pure diphosphinoxide (+) were obtained. The so obtained diphosphinoxide (+) has a $[\alpha]_D^{25}$=+316° value (c=0.41, solvent: benzene).

c) Resolution: diphosphinoxide (−)

From the filtrate resulting from the process of point a) described hereinabove the solvent was removed under reduced pressure, and a residue of 1.58 g was obtained and treated with 24 ml of NaOH 0.75N end extracted three times with 20 ml of $CH_2Cl_2$. The united organic phases were washed with 40 ml of water, then anhydrified on $Na_2SO_4$ and the solvent was removed under reduced pressure to afford 0.927 g of crude diphosphinoxide (−). The so obtained product was combined with 0.525 g of DBTA (+) and the whole was heated and dissolved with 35 ml of a solution constituted by AcOEt/CHCl$_3$ 20:15 (v/v). After 24 h, the mixture was filtered and there was obtained 0.603 g of a solid constituted by an adduct (VI) between diphosphinoxide (−) and DBTA (+) with $[\alpha]_D^{25}$=−67 (c=0.49, EtOH) and m.p.=165–185° C.

The adduct (VI) was deblocked as described under point b), obtaining diphosphinoxide characterised by $[\alpha]_D^{25}$=−265° (c=0.38, solvent: benzene).

The product was tritured with 2-propenol to give (−) diphosphinoxide $[\alpha]_D^{25}$=−310.2° (c=0.36, solvent:benzene).

EXAMPLE 5

Reduction 0.470 g of (+)-3-[(2-diphenylphosphinyl)phenyl]-2-diphenyl diphosphinyl-naphthothiophene as obtained under point b) of Example 4 was dissolved in 25 ml xylene and afterwards 1.1 ml Et$_3$N and 0.8 ml HSiCl$_3$ were added under inert conditions. The reaction mixture was heated for 3 h at 125° C., xylene and trichlorosilane were then removed under reduced pressure, the residue was treated with water and extracted with 3×20 ml $CH_2Cl_2$. The collected organic phases were anhydrified, the solvent was removed under reduced pressure and the so obtained raw material was dissolved with methyl alcohol. 0.35 g of (+)-3-[(2-diphenylphosphino)phenyl]-2-diphenylphosphine-naphtho thiophene was obtained that was characterized by a $[\alpha]_D^{25}$=+172° value (c=0.4, solvent: benzene).

$^1$H-NMR (CDCl$_3$): 6.9–7.9 (30H, m).

31P-NMR (CDCl$_3$): −14.25 (d, 1P), −25.3 (d, 1P).

The diphosphinoxide (−) as obtained under point c) of Example 4 was reduced to diphosphine by an analogous

EXAMPLE 6

Characterization of (IIIA, IIIB) and (IIA, IIB)

a) (±)-[(S)-dimethyl(a-methylbenzyl)aminate-$C^2N$][R, S)-3-{(2diphenylphosphino)phenyl}-2-diphenylphosphino-naphtho thiophene] palladium(II) chloride In a NMR tube, 13 mg of (−)di-$\mu$-chloro-bis [(S)-N,N-dimethyl (α-methylbenzyl)aminate-2-C,N]dipalladium (II) was added to a solution of 30 mg (R,S)-3-[(2-diphenylphosphino) phenyl]-2-naphthothiophene in $CDCl_3$. The reaction was monitored through TLC until the starting product had entirely disappeared. The $^{31}P$ NMR spectrum showed the formation of four isomers.

$^{31}P$ NMR ($CDCl_3$) (ppm): 6.70 (1P, d, J=40.9 Hz), 7.42 (1P, d, J=40.3 Hz), 12.23 (2P, d, J=41.5 Hz), 29.14 (1P, d, J=42.7 Hz), 36.40 (1P, d, J=40.3), 37.39 (1P, d, J=40.9).

b) (±)-[(S)-dimethyl(α-methylbenzyl)aminate-$C^2N$][R,S)-3-{(2diphenylphosphino)phenyl}-2-diphenylphosphino-4,6-dimethylbenzo[b]furan] palladium(II) chloride.

In a NMR tube, 17 mg of (−)di-$\mu$-chloro-bis[(S)-N,N-dimethyl (α-methylnaphthyl)aminate-2-C,N]dipalladium (II) was added to a solution of 30 mg (R,S)-3-[(2-dyphenylphosphino)phenyl]-2-4,6-dimethylbenzo[b]furan (IIA, IIB) in $CDCl_3$. The reaction was monitored through TLC until the starting product had entirely disappeared. The $^{31}P$ NMR spectrum showed the formation of four isomers.

$^{31}P$ NMR ($CDCl_3$) (ppm): 2.58 (1P, d, J=39.7 Hz), 3.83 (1P, extended d), 12.83 (1P, d, J=40.4 Hz), 20.95 (1P, d, J=41.2 Hz), 25.22 (1P, d, J=41.9 Hz), 37.43 (1P, d, J=39.70 Hz), 41.91 (1P, d, J=38.9 Hz).

EXAMPLE 7

Preparation of a [(+)-3-{(2-diphenylphosphino) phenyl}-2-diphenylphosphino-naphthothiophene) $RuCl_2]_n$ complex A test tube equipped with a side tap, an emery cone and a teflon-covered stirring bar, was repeatedly emptied and pressurised with argon; the operation was repeated 3 times. In the test tube were introduced, in the order, 14 mg of (+)chiral diphosphine as obtained in Example 5 (2.22 $10^{-2}$ mmoles), 4.5 mg of $[RuCl_2(C_6H_6)]n_2$ (1.8 $10^{-2}$ mmoles) and 5 ml of dimethylformamide freshly distilled in inert atmosphere and degassed with argon for 15 minutes. The red-brown suspension was heated to 100° C. for 15 minutes under stirring; the suspension quickly transformed into a clear yellow-orange solution. The solution was cooled to 50° C. and evaporated until it was dry. The residue was left under mechanical vacuum for one hour and subsequently pressurised with argon. The so obtained ruthenium complex was utilised without further purifications in the enantioselective reduction of ketoesters.

EXAMPLE 8

Preparation of a [(+)-3-{(2-diphenylphosphino) phenyl}-2-diphenylphosphino-naphthothiophene)Ru ($\eta^3$-2-methylallyl)$_2$] complex A test tube equipped with a side tap, an emery cone and a teflon-covered stirring bar, was repeatedly emptied and pressurised with argon; the operation was repeated at least 3 times. In the test tube were introduced, in the order, 15 mg of (+)chiral diphosphine as obtained in Example 5 (2.38 $10^{-2}$ mmoles), 6.9 mg of [(1,5-cyclooctadiene)Ru-bis-(metallyl)] (2.16 $10^{-2}$ mmoles) and 5 ml of toluene distilled and degassed with argon. The suspension was heated to 100° C. for 2 hours under magnetic stirring. At the end of the reaction a clear yellow-brown solution was obtained. The solution was cooled and evaporated until it was dry. The residue was left under mechanical vacuum for two hours and afterwards pressurised with argon. The ruthenium complex was utilised without further purifications in the reduction of α,β-unsaturated carboxylic acids.

EXAMPLE 9

Reduction of ethyl 3-oxo-butyrate to (R)-(−)-3-ethyl hydroxybutyrate

An autoclave from stainless steel, equipped with glass-liner, mechanical stirring and heating system was pressurised several times at 50 atm with hydrogen (the cycle was repeated at least 5 times) and thermostated at 40° C. At the catalyst prepared according to the method described in Example 7 was added 0.667 g (5.13 $10^{-3}$ moles) of ethyl 3-oxo-butyrate and 20 ml of a methyl alcohol/water mixture (99,5:0,5 v/v) previously degassed with argon for 30 minutes. The solution was transferred with a syringe into the autoclave which was pressurised to 100 atm. After 3 hours and 30 minutes, the autoclave was cooled, opened and the solvent was evaporated until it left an oily brown residue. A sample was analysed by GC (PEG 20 M column, oven temperature 100° C., FID and injector temperatures 200° C.); the result showed a quantitative conversion of the substrate. The residue was vacuum distilled at a temperature between 75 and 80° C. at 17 mmHg. The analysis of a sample of the purified product indicated that chemically pure ethyl 3-hydroxybutyrate had been obtained from the hydrogenation reaction.

$^1H$ NMR (200 Mhz, $CDCl_3$) (ppm): 4.2 (3H, superposed q and m), 2.4 (2H, d), 1.2 (6H, superposed t and d).

The enantiomeric excess was determined by HPLC (DAICEL CHIRACEL OD column, eluent: hexane-2-propanol 90:10 v/v, 1 ml/min) and resulted to be 96% in favour of the R enantiomer.

EXAMPLE 10

Reduction of ethylbenzylacetate to (S)-ethyl-3-hydroxy-3-phenylpropionate

An autoclave from stainless steel, equipped with glass-liner, mechanical stirring and heating system was pressurised several times at 50 atm with hydrogen (the cycle was repeated at least 5 times) and thermostated at 55° C. The preparation procedure of the catalyst was the same as the one of Example 7 (18.8 mg of (+)chiral diphosphine as obtained in Example 5 and 6.3 mg of $[RuCl_2(C_6H_6)]_2$) was utilized. To the catalyst were added 1.17 g of ethylbenzoylacetate (6.06 $10^{-3}$ moles) and 20 ml of a methyl alcohol/water mixture (99,5:0,5 v/v) previously degassed with argon for 30 minutes. The solution was transferred with a syringe into the autoclave which was pressurised to 100 atm. After 6 hours, the autoclave was cooled, opened and the solvent was evaporated until it left a liquid brown residue. A sample was analyzed by $^1H$ NMR and the analysis indicated a 64% conversion. The residue was purified with flash chromatography using a hexane:ethyl acetate mixture (70:30 v/v). The collected fractions were united and the solvent was evaporated; the product obtained resulted to be ethyl-3-hydroxy-3-phenylpropionate: $^1$H NMR (200 Mhz; $CDCl_3$) (ppm): 7.4–7.3 (5H, m), 5.1 (1H, d, d), 4.15 (2H, q), 3.3 (1H, s), 2.75 (2H, m), 1.25 (3H, t).

The enantiomeric excess was determined by HPLC (DAICEL CHIRACEL OD column, eluent: hexane: 2-propanol 90:10 v/v, 1 ml/min) and resulted to be 73% in favour of the S enantiomer.

EXAMPLE 11

Reduction of Atropic Acid to (R)(−)-2-phenylpropionic Acid

An autoclave from stainless steel, equipped with glass-liner, mechanical stirring and heating system was pressurised several times at 50 atm with hydrogen (the cycle was repeated at least 5 times) and thermostated at 45° C. To the catalyst prepared according to the method described for Example 8 were added 0.469 g of atropic acid (3.16 $10^{-3}$ moles) and 20 ml of methyl alcohol previously degassed with argon. The solution was transferred with a syringe into the autoclave which was pressurised to 52 atm. After 80 minutes, the autoclave was cooled, opened and the solvent was evaporated until it left an oily brown residue. A sample was analysed by $^1$H NMR; the analysis indicated a quantitative conversion of the substrate. The residue was purified with flash chromatography using a hexane:ethyl acetate mixture (70:30 v/v) containing 0.5% acetic acid. The solvent was evaporated from the collected fractions and the chemically pure reduction product was obtained.

$^1$H NMR (200 Mhz; $CDCl_3$) (ppm): 7.35 (5H, m), 3.75 (1H, q), 1.5 (3H, d).

The enantiomeric excess was determined by HPLC (RR WHELK column, eluent: hexane: 2-propanol: $CH_3COOH$ 99:1:0.5 v/v, 1 ml/min) and resulted to be 65% in favour of the R enantiomer.

EXAMPLE 12

Preparation and Use of a Complex [Rh(1,5-cyclooctadiene)$Cl_2$]/(+)diphosphine (IIIA, IIIB) for the Reduction of the Methyl Ester of 2-acetammidoacrylic Acid In a 250 ml pressure-resistant glass vessel containing diphosphine (IIIA, IIIB) (1.1 $10^{-2}$ mmoles) and [Rh(COD)Cl]$_2$ (5.$10^{-3}$ mmoles) under nitrogen, the solvent was added (10 ml of a 1:1 benzene/MeOH mixture). When all the solid was solubilised, the methyl ester of 2-acetammidoacrylic acid (1 mmole) was added.

The reactor was emptied from nitrogen by means of a mechanical pump, then pressurised with hydrogen at 3.7 atm and stirred at room temperature for 62 hours in a Parr hydrogenation apparatus. At the end of the reaction, the solvent was vacuum removed and the product purified by distillation (150° C. at 40 Pa).

Yield: 98%, enantiomeric purity 72%, S configuration.

The analysis of the conversion and the enantiomeric excess was carried out by gas chromatografy on Cyclodex-B chiral column, 20 m (isothermic at 105° C.; carrier gas He, 55 kpa). The retention times of the methyl ether of N-acetylamine are 24.0 and 24.7 minutes for the (R) enantiomer respectively the (S) enantiomer.

EXAMPLE 13

Preparation of 3-[(2-dicyclohexylphosphino)phenyl]-2-(dicyclohexylphosphino)naphthothiophene (VIIIA, VIIIB)

a) Preparation of 3-[(2-dicyclohexylphosphinyl)phenyl]-2-(dicyclohexylphosphinyl)naphthothiophene BuLi 2.5M (2.6 ml, prepared as in Example 2 was carefully dripped in a solution of 3-(o-bromophenyl) naphthothiophene (1 g) and TMEDA (1 ml) in THF (40 ml), cooled to −70° C. The temperature was allowed to raise and the reaction mixture was stirred for 1 hour at 20° C. Dicyclohexylchlorophosphine (1.5 g) was then dripped and stirred overnight. The solvent was removed under reduced pressure and the residue was treated with $H_2O$ (2 ml). $CH_2Cl_2$ (25 ml) and $H_2O_2$ (10 ml, 35%) were added. The mixture was stirred for 2 hours. Having separated the phases, the aqueous phase was extracted several times with metylene chloride; the organic phases were anhydrified ($Na_2SO_4$), and the solvent was removed under reduced pressure. The residue was chromatographied, using $AcOEtCH_2Cl_2$ (1:1) as eluent, obtaining 3-(2-dicyclohexylphosphinylphenyl)-2-dicyclohexyl phosphinyl naphthothiophene (0.7 g); m.p.=274° C.; M$^+$=684).

$^{31}$P-NMR ($CDCl_3$): 43.04 (1P, s, P on thiophene); 44.90 (1P, s, P on Ph).

$^1$H-NMR ($CDCl_3$): 0.5–2.5 (44H, m, cyclohexyl); 7.0–7.95 (10Hm, m, aromatic).

b) Preparation of 3-[(2-dicyclohexylphosphino)phenyl]-2-(dicyclohexylphosphino)naphthothiophene $HSiCl_3$ (0.20 ml) was carefully added to a solution of 3-(2-dicyclohexyl phopsphinyl phenyl)-2-dicyclohexyl phosphinyl naphtho thiophene (0.13 g) in xylene and triethylamine (0.25 ml), kept under argon atmosphere and stirred. The reaction mixture was kept at 100° C. for 1 hour, at 120° C. for 1 hour and at 140° C. for 1 hour. The solvent was removed under reduced pressure and the mixture was then treated with NaOH (10%, 10 ml) and heated to 60° C. for 15 min. The aqueous phase was extracted several times with degassed methylene chloride. The united organic phases were anhydrified ($Na_2SO_4$), and the solvent was removed under reduced pressure. The residue was treated with methyl alcohol to produce 3-(2-dicyclohexylphosphinophenyl)-2-dicyclohexyl phosphinonaphthothiophene (0.098 g).

(m.p.=200° C.$_{·DEC}$).

$^{31}$P-NMR ($CDCl_3$): −17.5 (1P, d, J=11 Hz); −9.54 (1P, d, J=11 Hz).

c) Resolution of 3-(2-dicylohexyl phosphinyl phenyl)-2-dicyclohexyl phosphinyl napthothiophene (±)-3-(2-dicylchexyl phosphinyl phenyl)-2-dicyclohexyl phosphinyl napthothiophene (0.52 g) and (−)-O,O'-dibenzoyl-L-tartaric acid (0.28 g) were dissolved in a mixture of chloroform/$Et_2O$ 1:5 (10 ml) and reflow-heated for 5 minutes. After 24 hours, there was recuperated by filtration an adduct between (−)-diphosphinoxide and (−)-DBTA (0.270 g), $[\alpha]_D^{25}$=−45.8° (c=0.33, EtOH). The adduct was cleaved by treatment with diluted sodium carbonate 0.75N (5 ml), and (−)-diphosphineoxide was exhaustively extracted with methylene chloride. The united organic phases were washed with water, anhydrified ($Na_2SO_4$) and the solvent was removed under reduced pressure. The residue was treated with $iPr_2O$ to produce (−)-3-(2-dicyclohexylphosphinylphenyl)-2-dicyclohexyl phosphinyl naphthothiophene (0.07 g). $[\alpha]_D^{25}$=−71° (c=0.31, $C_5H_6$).

EXAMPLE 14

Preparation of 3-[(2-dicyclohexyl phosphino)phenyl]-2-(diphenylphosphino)naphthothiophene (VIA, VIB)

a) Preparation of 3-[(2-dicyclohexyl phosphino)phenyl]-2-(diphenylphosphino) naphthothiophene LDA (LithioDiisopropyilAmine) (0.0117 moles) was carefully dripped in a solution of 3-(o-bromophenyl) naphthothiophene (4 g) in THF (170 ml), cooled to −70° C. The mixture was kept at −70° C for 15 minutes, then the temperature was allowed to increase up to −40° C., and diphenylchlorophosphine (2.16 ml, 0.017 moles) was dripped under stirring for 30 minutes. The temperature was allowed to increase up to the room temperature. The solvent was removed under reduced pressure, the residue was treated with $H_2O$ (8 ml) and $CH_2Cl_2$ (80 ml) and $H_2O_2$ (15 ml, 35%) was added. The mixture was stirred for 2 hours. Having separated the phases, the aqueous phase was extracted several times with metylene chloride; the organic phases are anydrified ($Na_2SO_4$), and the solvent was removed under reduced pressure. The residue was treated with ACOEt, to produce 3-o-bromophenyl)-2-diphenylphosphinylnapthothiophene (4.38 g, m.p.=193°, $M^+$539).

Elementary analysis: C=66.33%; H=3.66%

$^{31}$P-NMR (CDCl$^3$): 19.15 (1P, s);

$^1$P-NMR (CDCl$^3$): 7.1–7.9 (20H, M, arom).

b) Preparation of 3-(2-cyclohexylphosphinylphenyl)-2-diphenyl phosphinylnaphthothiophene t-BuLi (2.5 ml, 1.5M) was carefully dripped in a solution of 3-(o-bromophenyl)-2-diphenylphosphinyl naphthothiophene (1 g) in $Et_2O$ (40 ml), cooled to −78° C. The temperature was allowed to increase up to 10° C. and dicyclohexylchlorophosphine (0.013 moles) was dripped. The mixture was kept at room temperature for 5 hours. The solvent was removed under reduced pressure, the residue treated with $H_2O$ (3 ml) and $CH_2Cl_2$ (30 ml) and $H_2O_2$ (4 ml, 35%) was added. The mixture was stirred for 2 hours. Having separated the phases, the aqueous phase was extracted several times with methylene chloride; the united organic phases are anhydrified ($Na_2SO_4$), and the solvent was removed under reduced pressure. The residue was chromatographied using $CH_2Cl_2$:ACOEt (3:7) as eluent. The isolated product was treated with $iPr_2O$ to obtain 3-(2-dicyclohexylphospinyl phenyl)-2-diphenyl phosphinylnaphthothiophene (0.5 g, m.p. 242° C., $N^+$=672).

$^{31}$P-NMR (CDCl$_3$): 28.7 (0.8P, s); 44.16 (1,2P, s);

$^1$H-NMR (CDCl$_3$): 0.7–2.1 (22H, m, cycloexhyl); 6.7–7.9 (20H, m, arom).

c) Preparation of 3-(2-dicyclohexylphosphinophenyl)-2-diphenylphosphinonapthothiophene HSiCL$_3$ (0.24 ml) was carefully added to a solution of 3-(2-dicyclohexylphosphinylphenyl)-2-diphenylphosphinonaphthothiophene (0.2 g)) in xylene (6 ml) and triethylamine (0.35 ml) kept in argon atmosphere and under stirring. The reaction mixture was kept at 100° C. for 1 hour, at 120° C. for 1 hour and at 140° C. for 2 hours. The solvent was removed under reduced pressure and the mixture was then treated with NaOH (10%, 15 ml) and heated to 60° C. for 15 min. The aqueous phase was extracted several times with degassed methylene chloride. The united organic phases were anhydrified ($Na_2SO_4$), and the solvent was removed under reduced pressure. The residue was treated with methyl alcohol to produce 3-(2-dicyclohexylphosphinophenyl)-2-diphenylphosphinonaphthothiophene (0.12 g, m.p.157° C.$_{DEC}$).

$^{31}$P-NMR (CDCl$_3$):−18.23 (1.2P, s); −16.23 (0.8P, s);

$^1$H-NMR (CDCl$_3$): 0.7–2.0 (22H, m, cycloexhyl); 6.65–7.85 (20H, m, arom).

EXAMPLE 15

Reduction of ethyl cyclopentanonecarboxylate with {[(−)-3-(2-diphenylphosphinophenyl)-2-diphenylphosphino naphthothiophene]RuCl$_2$(DMF)]}$_n$ In a tailed test tube, in inert atmosphere, containing {[(−)-3-(2-diphenylphosphinophenyl)-2-diphenylphosphino naphthothiophene]RuCl$_2$(DMF}]}$_n$ (0.016 mmoles) a solution of ethyl cyclopenthanonecarboxylate (2.50 g; 16 mmoles) dissolved in MeOH/H$_2$O (30 ml/0.5 ml) was introduced. The obtained solution was injected in an autoclave previously hydrogen-acclimatised. The reduction was carried out at 100 atm and 40° C. for 8 hours under stirring. The solution was collected, MeOH was removed under reduced pressure and the aqueous phase extracted with $CH_2Cl_2$. The united organic phases were anhydrified ($Na_2SO_4$), and the solvent was removed under reduced pressure.

The $^1$H-NMR analysis of the reaction raw product indicated that the conversion to ethyl 2-hydroxycyclopentanonecarboxylate was complete.

The product was purified by chromatography with hexane/AcOEt as eluent in a 6:4 ratio.

The enantiomeric excesses were determined by HPLC on chiral stationary phase (CHIRACEL OD; hexane/isopropanol (9/1); flow: 1 ml/min) and resulted to be 97% for the anti stereoisomer; the diastereoisomeric excess, determined by gascromatography analysis, is 74% in favour of the trans diastereoisomer.

EXAMPLE 16

Reduction of ethyl cyclopentanonecarboxylate with {[(±)-3-(2-dicyclohexylphosphino phenyl)-2-dicyclohexyl phosphino nafthothiophene]RuCl$_2$ (DMF)}$_n$ In a tailed test tube, in inert atmosphere, containing {[(±)-3-(2-dicyclohexylphosphino phenyl)-2-dicyclohexyl phosphino nafthothiophene]RuCl$_2$(DMF)}$_n$ (0.0076 mmoles) a solution of ethyl cyclopenthanoneoncarboxylate (1.15 g; 7.4 mmoles) dissolved in MeOH/H$_2$O (30 ml/0.5 ml) was introduced. The obtained solution was injected in an autoclave previously hydrogen-acclimatised. The reduction was carried out at 100 atm and 50° C. for 28 hours under stirring. The solution was collected, MeOH removed under reduced pressure and the aqueous phase extracted with $CH_2Cl_2$. The united organic phases were anhydrified ($Na_2SO_4$), and the solvent was removed under reduced pressure.

The $^1$H-NMR analysis of the reaction raw product indicated that that the conversion in ethyl 2-hydroxycyclopentanecarboxylate was complete.

The diastereoisomeric excess, determined by gascromatographic analysis, was 66% in favour of the trans diastereoisomer.

EXAMPLE 17

Reduction of ethyl cyclopentanonecarboxylate with {[(±)-3-(2-dicyclohexylphosphino phenyl)-2-diphenyl phosphino naphthothiophene]RuCl$_2$(DMF)}$_n$ In a tailed test tube, in inert atmosphere, containing {[(±)-3-(2-dicyclohexylphosphino phenyl)- 2-diphenyl phosphino naphthothiophene]RuCl$_2$(DMF)}$_n$ (0.0078 mmoles) a solution of ethyl cyclopenthanonecarboxylate (1.2 g; 7.68 mmoles) dissolved in MeOH/H$_2$O (23 ml/0.5 ml) was introduced. The obtained solution was injected in an autoclave previously hydrogen-acclimatised. The reduction was carried out at 100 atm and 45° C. for 30 hours under stirring. The solution was collected, MeOH removed under reduced pressure and the aqueous phase extracted with CH$_2$Cl$_2$. The united organic phases were anhydrified (Na$_2$SO$_4$), and the solvent was removed.

The $^1$H-NMR analysis of the reaction raw product indicated that that the conversion in ethyl 2-hydroxy-cyclopentanonecarboxylate is complete.

The diastereoisomeric excess, determined by gascromatographic analysis, is 45% in favour of the trans diastereoisomer.

What is claimed is:

1. A diphosphine of a mixed heteroarylic-arylic type having the following general formula:

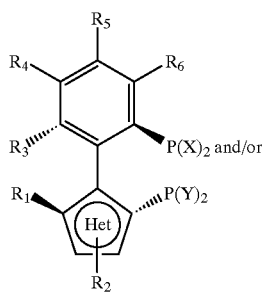

(IA)

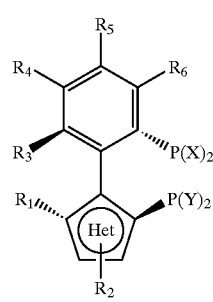

(IB)

wherein:

X=Y or X≠Y, and X, Y are selected from among linear or branched C$_3$–C$_{10}$ alkyl, cyclic C$_5$–C$_6$ alkyl, phenyl, aryl, substituted phenyl or aryl, wherein the substituents are selected from among linear or branched C$_1$–C$_{10}$, halogen, OR$_7$, wherein R$_7$ is hydrogen, linear or branched C$_1$–C$_{10}$ alkyl;

R$_1$ is selected from among linear or branched C$_1$–C$_{10}$ alkyl, cyclic C$_5$–C$_6$ alkyl, OR$_{11}$, with R$_{11}$ is equal to hydrogen, linear or branched C$_1$–C$_{10}$ alkyl, NR$_{12}$R$_{13}$, wherein R$_{12}$ and R$_{13}$ may be equal or different, and selected from among linear or branched C$_1$–C$_{10}$ alkyl, phenyl, aryl, substituted phenyl or aryl, wherein substituents are selected from among linear or branched C$_1$–C$_{10}$ alkyl, halogen, OR$_7$, wherein R$_7$ is hydrogen, linear or branched C$_1$–C$_{10}$ alkyl;

R$_2$ is selected from among hydrogen, linear or branched C$_1$–C$_{10}$ alkyl, cyclic C$_5$–C$_6$ alkyl, phenyl, aryl, substituted phenyl or aryl, wherein substituents are selected from among linear or branched C$_1$–C$_{10}$ alkyl, halogen, OR$_7$, wherein R$_7$ is hydrogen, linear or branched C$_1$–C$_{10}$ alkyl;

COOR$_{10}$, wherein R$_{10}$ is linear or branched C$_1$–C$_{10}$ alkyl, NR$_{12}$R$_{13}$, wherein R$_{12}$ and R$_{13}$ may be equal or different, and selected from among linear or branched C$_1$–C$_{10}$ alkyl, OR$_{11}$ with R$_{11}$ selected as equal to hydrogen, linear or branched C$_1$–C$_{10}$ alkyl;

or the 5-atom heterocyclic aromatic ring is condensated to a benzene ring or a substituted or non substituted naphthalene ring, wherein the substituents are selected from among linear or branched C$_1$–C$_{10}$ alkyl, cyclic C$_5$–C$_6$ alkyl, halogen, and in this case either R$_1$ or R$_2$ or the both of them may be part of said benzene or naphthalene ring;

R$_3$, R$_4$, R$_5$, R$_6$ may be equal or different and are selected from among hydrogen, linear or branched C$_1$–C$_{10}$ alkyl, cyclic C$_5$–C$_6$ alkyl, halogen, OR$_{11}$ with R$_{11}$ selected as equal to hydrogen, linear or branched C$_1$–C$_{10}$ alkyl, SO$_3$H or a corresponding salt, NR$_{12}$R$_{13}$ wherein R$_{12}$ and R$_{13}$ may be equal or different, and selected from among linear or branched C$_1$–C$_{10}$ alkyl, or R$_{12}$ and R$_{13}$ form with the N atom a morpholinic, pyrrolidonic, piperidinic ring or a couple of the adjoining R$_3$ to R$_6$ substituents represents a benzene ring wherein the substituents are selected from among linear or branched C$_1$–C$_{10}$ alkyl, cyclic C$_5$–C$_6$ alkyl, halogen, condensated to the aryl ring of said diphosphine.

2. The chiral diphosphine according to claim 1, comprising a radical of a 5-atom heterocyclic aromatic ring united to the radical of an aromatic carbocyclic ring, said radical of said 5-atom heterocyclic aromatic ring being selected from among:

furyl thienyl pyrrolyl, 2-imidazolyl and the corresponding benzocondensates, 5- pirazolyl 2-[1,3,4-triazolyl]

4-thiazolyl 4-isoxazolyl.

3. The chiral diphosphine according to claim 2, characterised in that said 5-atom heterocyclic aromatic ring is condensated to a benzene ring or a possibly substituted naphthalene ring, wherein the substituents are selected from among linear or branched C$_1$–C$_{10}$ alkyl, cyclic C$_5$–C$_6$ alkyl, halogen, and in this case either R$_1$ or R$_2$ or the both of them may be part of said benzene or naphthalene ring, and in that said carbocyclic aromatic ring is condensated to a benzene ring or a possibly substituted naphthalene ring, wherein the substituents are selected from among linear or branched C$_1$–C$_{10}$ alkyl, cyclic C$_5$–C$_6$ alkyl, halogen.

4. The chiral diphosphine according to claim 1, having the following formula:

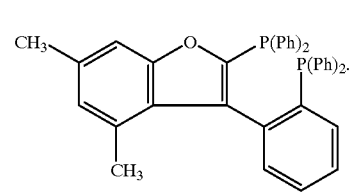

(IIA, IIB)

5. The chiral diphosphine according to claim 1, having the following formula:

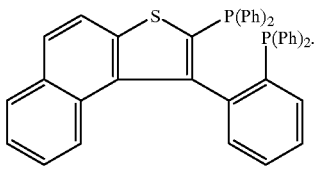

(IIIA, IIIB)

6. The chiral diphosphine according to claim 1, having the following formula:

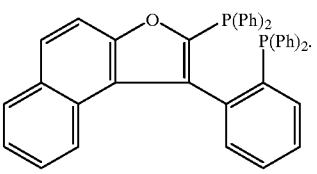

(IVA, IVB)

7. The chiral diphosphine according to claim 1, having the following formula:

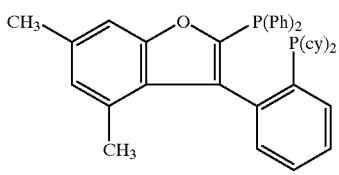

(VA, VB)

where cy means cyclohexyl.

8. The chiral diphosphine according to claim 1, having the following formula:

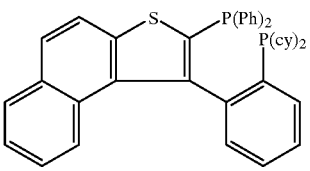

(VIA, VIB)

where cy means cyclohexyl.

9. The chiral diphosphine according to claim 1, having the following formula:

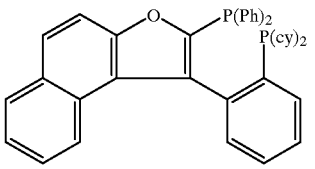

(VIIA, VIIB)

where cy means cyclohexyl.

10. The chiral diphosphine according to claim 1, characterised in that said X and Y are different from one another and selected from among: linear or branched $C_3$–$C_{10}$ alkyl, cyclic $C_5$–$C_6$ alkyl, phenyl, aryl, substituted phenyl or aryl, wherein the substituents are selected from among linear or branched $C_1$–$C_{10}$, halogen, $OR_7$, wherein $R_7$ is hydrogen, linear or branched $C_1$–$C_{10}$ alkyl.

11. The chiral diphosphine according to claim 1, characterised in that said X and Y are equal to one another and selected from among: linear or branched $C_3$–$C_{10}$ alkyl, cyclic $C_5$–$C_6$ alkyl, phenyl, aryl, substituted phenyl or aryl, wherein the substituents are selected from among linear or branched $C_1$–$C_{10}$, halogen, $OR_7$, wherein $R_7$ is hydrogen, linear or branched $C_1$–$C_{10}$ alkyl.

12. A process for the preparation of heteroarylic-arylic chiral dophosphines according to claim 1, characterised in that it comprises the following steps:
  synthesis according to methods of a known type of an ortho-halogen-arylheterocyclic system, wherein the heterocyclic system has the position adjoining the inter-ring bond, that can be metallated,
  a first metallation reaction of said position adjoining the inter-ring bond or metal-halogen exchange reaction of halogen on the aryl ring, obtaining a metallated aryl-heterocyclic system,
  reaction of said metallated system with a chlorophosphine or a phosphinyl chloride, obtaining a phosphinic heteroaryl system or phosphinylic heteroaryl system,
  a second reaction of metal-halogen exchange of halogen on the arylic ring or metallation reaction of said position adjoining the inter-ring bond, obtaining a heteroaryl phosphinic system or a heteroaryl phosphinylic metallated system,
  reaction of said heteroaryl phosphinic system or a heteroaryl phosphinylic metallated system with a chlorophosphine or a phosphinyl chloride, obtaining a heteroaryldiphosphinic, heteroarylphosphinylic or heteroaylphosphinic phosphinylic racemic system,
  possible conversion of said heteroaryldiphosphinic, heteroarylphosphinylic or heteroaylphosphinic phosphinylic racemic system into a heteroaryldiphosphinylic racemic system by oxidation reaction according to known techniques,
  reaction of said heteroaryldiphosphinylic racemic system with an acid resolving chiral agent, obtaining two diastereoisomeric adducts,
  separation of said diastereoisomeric adducts by fractionated crystallisation,
  basic treatment of each of said separated diastereoisomeric adducts, obtaining the corresponding enantiomerically pure heteroaryldiphosphinic system,
  reduction of said enantiomerically pure heteroaryldiphosphinic system with reducing agents of a known type, obtaining an enantiomerically pure heteroaryldiphosphinic chiral system (IA) (IB).

13. The process according to claim 12, characterised in that said reactions of metallation and metal-halogen exchange take place simultaneously, obtaining directly a bis-metallated system.

14. The process according to claim 12, characterised in that said reducing agents are silanes.

15. The process according to claim 12, characterised in that said racemic heteroaryldiphosphinic system is directly resolved by column chromatography, using chiral stationary phase or chiral eluent.

16. The process according to claim 12, characterised in that said solving agent is selected from among dibenzoyltartaric acid, ditolyltartaric acid, camphosulfonic acids.

17. A method of using heteroarylic-arylic chiral diphosphines according to claim 1, as chiral ligands for the preparation of complexes with transition metals.

18. A chiral complex comprising at least a heteroarylic chiral diphosphine according to claim 1 as ligand and at least a transition metal.

19. The chiral complex according to claim 18, characterised in that said said metal is selected from among Ru, Rh, Pd, Pt, Ir, Ni.

20. A process for the preparation of chiral complexes according to claim 18, comprising an exchange reaction between said heteroarylic chiral diphosphine and a complex of said metal co-ordinated to a ligand by means of a labile co-ordination bond.

21. The process according to claim 20, characterised in that said ligand is selected from among 1,5-cis, cis-cyclooctadiene, norbonadiene, (ethylene)$_2$, triarylstibine, benzonitrile, bismetallyl.

22. The process according to claim 20, characterised in that it is carried out by using a solvent selected from among chlorinated solvents, alcohols, aromatic hydrocarbons, ethers, dimethyl formamide.

23. A method of using chiral complexes according to claim 1 as chiral catalysts for stereocontrolled reactions.

24. Chiral catalysts for stereocontrolled reactions comprising at least a complex between a heteroarylic chiral diphosphine according to claim 1 and a transition metal.

25. A method of using chiral catalys according to claim 24 for the realization of stereocontrolled reactions.

26. A process for conducting stereocontrolled reactions comprising using the chiral catalysts according to claim 24.

27. The process for conducting stereocontrolled reactions according to claim 26, wherein said reactions are diastereo- and enantioselective reduction reactions.

28. The process for conducting stereocontrolled reactions according to claim 27, wherein each reaction comprises a reaction of reduction of olefins (—C=C—), reduction of ketone carbonyl groups (—C=O), reduction of imine groups (—C=N—), reduction of enamines (—N—C=C—).

29. The process for conducting stereocontrolled reactions according to claim 26, wherein said reactions comprise hydroformylation reactions.

30. The process for conducting stereocontrolled reactions according to claim 26, wherein said reactions comprise hydrocyanation reactions.

31. The process for conducting stereocontrolled reactions according to claim 26, wherein said reactions comprise double bond isomerization reactions.

32. The process for conducting stereocontrolled reactions according to claim 26, wherein said reactions comprise carbon—carbon bond formation reactions.

33. The process for conducting stereocontrolled reactions according to claim 26, wherein said reactions comprise hydrocyanation reactions.

34. The process for conducting stereocontrolled reactions according to claim 26, wherein said reactions comprise hydrosilylation reactions.

35. The chiral diphosphine according to claim 1, having the following formula:

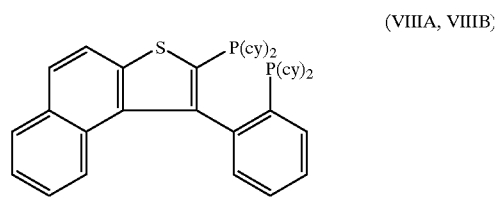

(VIIIA, VIIIB)

where cy means cyclohexyl.

36. The chiral diphosphine according to claim 1, comprising a radical of a 5-atom heterocyclic aromatic ring united to the radical of an aromatic carbocyclic ring, said radical of said 5-atom heterocyclic aromatic ring being selected from the group consisting of furyl and thienyl.

37. The chiral diphosphine according to claim 36,
wherein said radical of said 5-atom heterocyclic aromatic ring is furyl.

38. The chiral diphosphine according to claim 36,
wherein said radical of said 5-atom heterocyclic aromatic ring is thienyl.

39. The chiral diphosphine according to claim 1, comprising a radical of a 5-atom heterocyclic aromatic ring united to the radical of an aromatic carbocyclic ring, said radical of said 5-atom heterocyclic aromatic ring being selected from the group consisting of furyl, thienyl, and pyrrolyl.

40. The chiral diphosphine according to claim 39,
wherein said radical of said 5-atom heterocyclic aromatic ring is furyl.

41. The chiral diphosphine according to claim 39,
wherein said radical of said 5-atom heterocyclic aromatic ring is thienyl.

42. The chiral diphosphine according to claim 39,
wherein said radical of said 5-atom heterocyclic aromatic ring is pyrrolyl.

* * * * *